United States Patent
Fujiwara et al.

[11] Patent Number: 6,034,043
[45] Date of Patent: Mar. 7, 2000

[54] MILD ANTIMICROBIAL LIQUID CLEANSING FORMULATIONS COMPRISING POLYVALENT CATION OR CATIONS FOR IMPROVING AN ANTIMICROBIAL EFFECTIVENESS

[75] Inventors: Mitsuko Fujiwara, Edgewater; Carol Vincent, Wanaque, both of N.J.; Kavssery Ananthapadmanabhan, New Windsor, N.Y.

[73] Assignee: Lever Brothers Company, Division of Conopco, Inc., New York, N.Y.

[21] Appl. No.: 09/294,953

[22] Filed: Apr. 20, 1999

[51] Int. Cl.[7] .............................. A61K 7/50; C11D 7/50; C11D 17/00; C11D 9/00
[52] U.S. Cl. ..................... 510/130; 510/159; 510/426; 510/428; 510/501; 510/502; 510/508
[58] Field of Search ...................... 510/130, 159, 510/426, 428, 501, 502, 508

[56] References Cited

U.S. PATENT DOCUMENTS

| | | |
|---|---|---|
| 3,761,418 | 9/1973 | Parran, Jr. . |
| 3,835,057 | 9/1974 | Cheng . |
| 3,992,146 | 11/1976 | Fazzalari . |
| 4,022,880 | 5/1977 | Vinson et al. . |
| 4,332,791 | 6/1982 | Raaf et al. . |
| 4,656,031 | 4/1987 | Lane et al. . |
| 4,714,563 | 12/1987 | Kajs et al. . |
| 4,923,619 | 5/1990 | Legros . |
| 5,037,634 | 8/1991 | Williams et al. . |
| 5,312,934 | 5/1994 | Letton . |
| 5,389,279 | 2/1995 | Au et al. . |
| 5,486,307 | 1/1996 | Misselyn et al. . |
| 5,540,853 | 7/1996 | Trinh et al. ......................... 510/101 |

FOREIGN PATENT DOCUMENTS

92/18100  10/1992  WIPO .

*Primary Examiner*—Necholus Ogden
*Attorney, Agent, or Firm*—Ronald A. Koatz

[57] ABSTRACT

The present invention relates to liquid skin cleansing compositions comprising (1) mild surfactant systems; (2) 0.1 to 10% by wt. of a polyvalent cation or cations selected from the group consisting of zinc, copper, tin, aluminum cobalt, nickel, chromium, titanium and/or manganese and mixture thereof; and (3) 1% to 99% water wherein said cation or cations provide antibacterial activity. In a second embodiment of the invention, the cation or cations potentiates antibacterial effect in compositions already containing an antibacterial agent. In a third embodiment, the invention relates to a method of enhancing antibacterial effect using these polyvalent cation or cations.

4 Claims, 4 Drawing Sheets

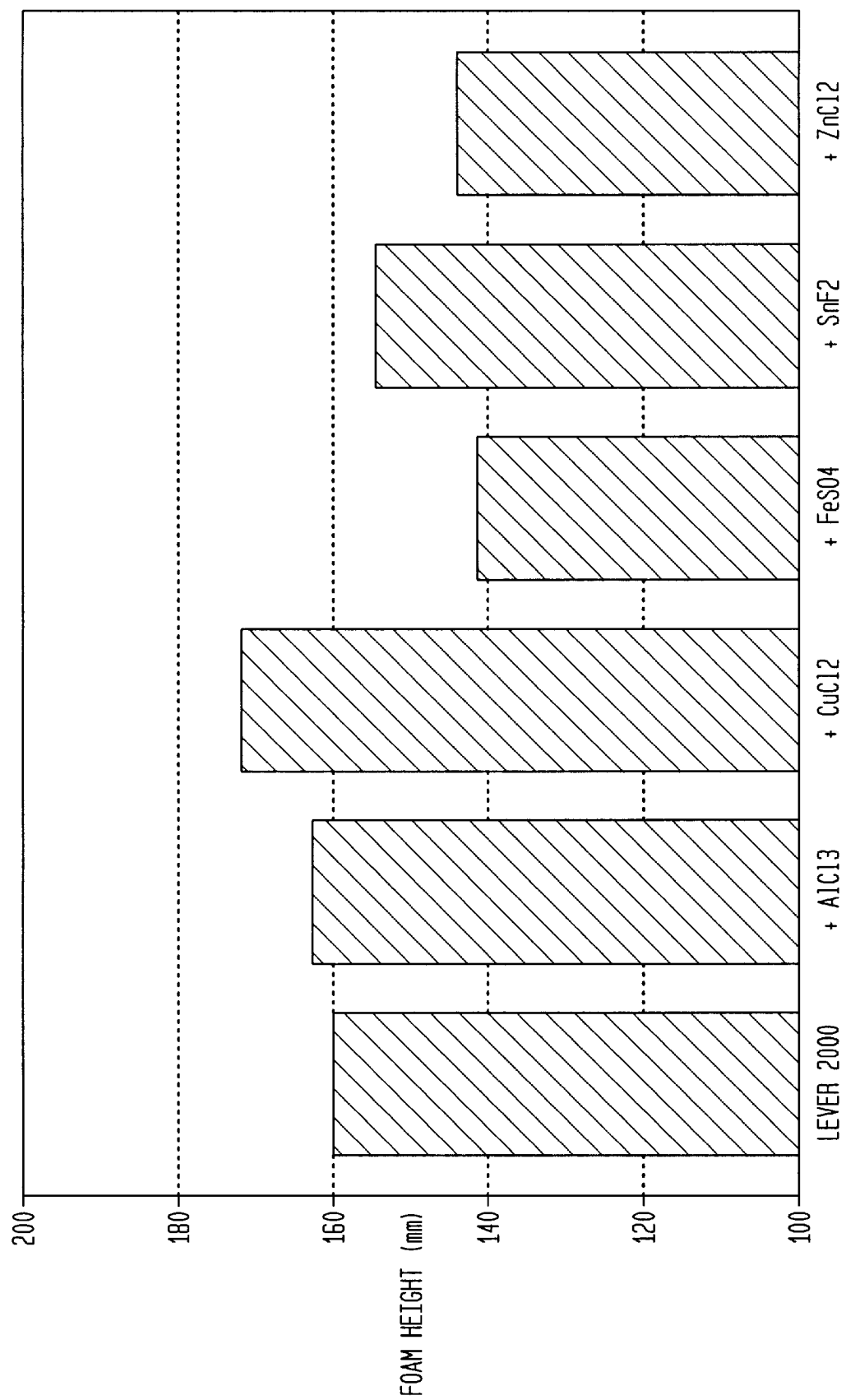

MILD ANTIMICROBIAL LIQUID CLEANSING FORMULATIONS COMPRISING POLYVALENT CATION OR CATIONS FOR IMPROVING AN ANTIMICROBIAL EFFECTIVENESS

BACKGROUND OF THE INVENTION

The present invention relates to liquid cleansing compositions having enhanced antimicrobial effectiveness. More specifically, the invention relates to specific polyvalent metal ions which improve antibacterial activity when used in liquid cleansing formulations. Neither the metals alone or the compositions alone provide the observed effect.

There is a large demand in the market for mild liquid cleansing formulations which additionally have an antibacterial effect. Antibacterial cleansers are preferred because they kill germs and mild personal cleansers are preferred to minimize skin irritation, dryness, etc. However, the combination of mild cleansing formulations and strong antibacterial effect is difficult to achieve. Thus, for example, while soaps provide antibacterial effects, they are not mild to the skin. When very mild non-soap surfactants are used, antibacterial effect is greatly compromised.

The balancing act between providing mildness and antibacterial effectiveness is recognized for example in International Publication WO 92/18100. In this publication, improved clinical mildness is said to be provided through the use of a water soluble cationic polymer (see page 10, lines 24–29). Cationic polymer is apparently used instead of additional ethoxylated surfactant because the percent of mild ethoxylated surfactant must be minimized in order not to affect antibacterial effectiveness (page 7, lines 4–6).

Another approach to providing mildness effect without affecting antibacterial properties is that which appears to be used by Dial in, for example, Liquid Dial Plus with Moisturizers Antibacterial Soap$^{(R)}$. Here, mildness benefits are apparently provided by the use of moisturizing compounds rather than by the use of very mild surfactants alone (which, as indicated above, compromises antibacterial effectiveness).

In both cases, it can be readily seen that it is extremely difficult to provide effective antibacterial action in the presence of very mild surfactants. Rather, it is necessary to minimize the presence of those mild surfactants, by using larger amounts of harsher surfactants or soaps, and to mask the effects of the harshness by providing cationic mildness conditioning agents (WO 92/18100) or moisturizers (as in the Dial product).

It would be greatly beneficial if antibacterial effectiveness could be provided by polyvalent metal cation or cations which alone or together provide synergistic antimicrobial efficacy when used with liquid cleansing formulations (which themselves may or may not already contain an antibacterial agent), even in compositions with very mild surfactant systems.

Polyvalent cations such as zinc, copper, tin and aluminum are known antimicrobial agents and have long been used in cosmetic, dental and pharmaceutical applications (see, for example, S. S. Block, "Sterilization and Preservation", 1983; JP 63,250,309 and U.S. Pat. No. 5,037,634 to Williams et al.; see also U.S. Pat. No. 4,332,791 to Raaf et al.)

In particular, cations such as zinc ions have long been used in compositions for inhibiting plaque and/or calculus formation (U.S. Pat. No. 4,022,880 to Vinson et al. and U.S. Pat. No. 4,656,031 to Lane et al.). Copper ions have been used to stop fungal growth in bathtubs and ceramics (U.S. Pat. No. 3,992,146) and, in general, as disinfectants (U.S. Pat. No. 4,923,619).

In none of these references is it taught or suggested that one or more polyvalent metal cation or cations be used, i.e., in mild, liquid skin cleansing compositions by acting synergistically with the mild compositions to provide antibacterial activity.

Unexpectedly, applicants have now found that one or more polyvalent cation or cations (i.e., zinc, copper, tin, iron aluminum, cobalt, nickel, chromium, titanium and/or manganese) may be used to synergistically provide an antibacterial effect when used in mild, liquid skin cleansing compositions.

BRIEF SUMMARY OF THE INVENTION

The present invention relates to liquid skin cleansing compositions comprising:

(1) any mild surfactant system (i.e., any one or more surfactants which alone or together are demonstrated by clinical tests to be milder than soap itself) in an amount of from about 1–99% by wt., preferably 2–85% by wt., more preferably 3–40% by wt. surfactant system; wherein at least 10%, preferably at least 25% (up to 100%, if desired) of the surfactant system comprises anionic surfactant;

(2) 0.1 to 10%, preferably 0.1 to 5%, more preferably 0.5 to 5.0% by weight of polyvalent cation or cations selected from the group consisting of zinc, copper, tin, iron, aluminum, cobalt, nickel, chromium, titanium, manganese and mixtures thereof; and (3) 1% to 99% by wt., preferably 15 to 97%, most preferably 60 to 97% by wt. water.

In a second embodiment of the invention, the liquid skin cleansing composition comprises 0.001% to 5% by weight of an antibacterial agent and the polyvalent cation or cations act to potentiate the antimicrobial effect of the composition.

BRIEF DESCRIPTION OF THE DRAWINGS

FIG. 5 shows that the metal salts do not affect foaming ability of the compositions when added to a typical mild, cleansing composition.

DETAILED DESCRIPTION OF THE INVENTION

Figure 1:
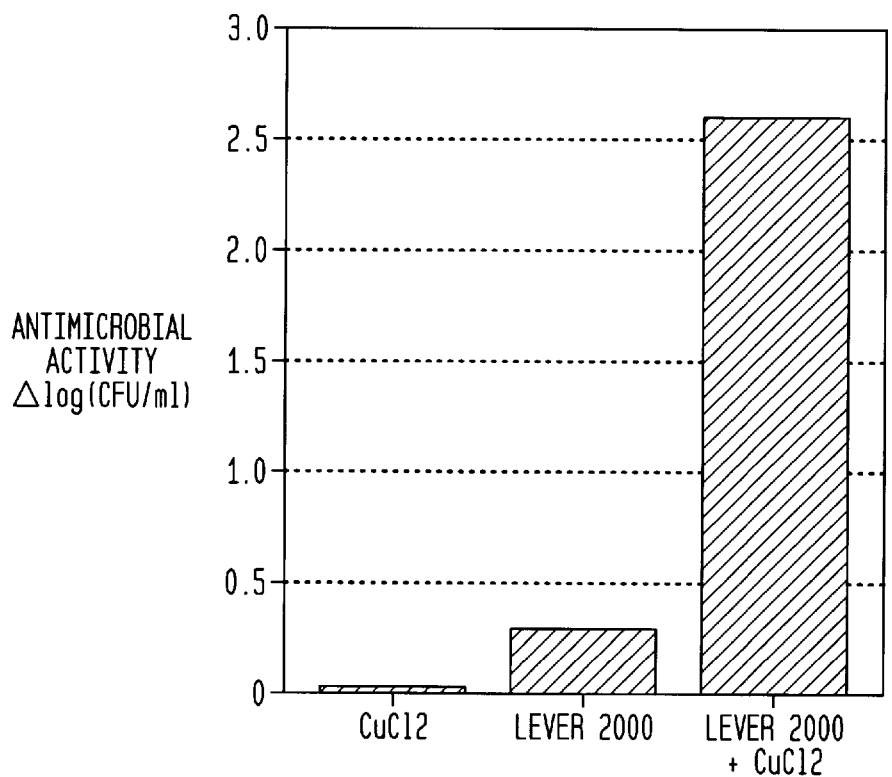
FIG. 1 shows the synergistic effect of metal cation in a typical mild skin cleansing formulation of the invention.

The present invention relates to liquid skin cleansing compositions comprising 1 to 99% by weight, preferably 2 to 85%, more preferably 3 to 40% of a mild surfactant system comprising one or more surfactants which alone or together have been clinically tested to be milder than soap itself as measured by zein solubilization test (soap yields 80% zein solubilized). Preferably, the mildness is such that zein solubilization is in the range 10–60%. At least 10%, preferably at least 25% of the surfactant composition must be anionic surfactant. In theory, as long as the anionic is milder than soap itself, 100% of the surfactant composition may be anionic.

A number of anionic, nonionic, cationic and amphoteric surfactants may be employed in the surfactant system of the invention provided of course that the surfactant, if used alone, or surfactant mixture is milder than would be soap itself as measured by the zein solubilization test.

Among suitable anionic co-actives are the alkyl ether sulfates, acyl isethionates, alkyl ether sulfonates, sarcosinates, sulfosuccinates, taurates and combinations thereof. Among suitable amphoteric co-actives may be included alkylbetaines, amidopropyl betaines, amidopropyl sultaines and combinations thereof.

Alkyl ether sulfates of the present invention will be of the general formula R—(OCH$_2$CH$_2$)$_n$OSO$_3$—M$^+$ wherein R ranges from C$_8$–C$_{20}$ alkyl, preferably C$_{12}$–C$_{15}$alkyl, n is an integer from 1 to 40, preferably from 2 to 9, optimally about 3, and M$^+$ is a sodium, potassium, ammonium or triethanolammonium cation.

Typical commercial co-actives of this variety are listed in the Table below:

| Trademark | Chemical Name | Physical Form | Manufacturer |
|---|---|---|---|
| Steol CS 330 | Sodium Laureth Sulfate | Liquid | Stepan |
| Standopol ES-3 | Sodium Laureth Sulfate | Liquid | Henkel |
| Alkasurf ES-60 | Sodium Laureth Sulfate | Paste | Alkaril |
| Cycoryl TD | TEA Laureth Sulfate | Paste | Cyclo |
| Standapol 125-E | Sodium Laureth-12 Sulfate | Liquid | Henkel |
| Cedepal TD407MF | Sodium Trideceth Sulfate | Paste | Miranol |
| Standopol EA-2 | Ammonium Laureth Sulfate | Liquid | Henkel |

Alkyl ether sulfonates may also be employed for the present invention. Illustrative of this category is a commercial product known as Avenel S-150 commonly known as a sodium C$_{12}$–C$_{15}$ Pareth-15 sulfonate.

Another co-active type suitable for use in the present invention is that of the sulfosuccinates. This category is best represented by the monoalkyl sulfosuccinates having the formula RO$_2$CCH$_2$CH(SO$_3$—Na$^+$)COO—M$^+$; and amido-MEA sulfosuccinates of the formula: RCONHCH$_2$CH$_2$O$_2$CCH$_2$CH(SO$_3$—M$^+$)COO—M$^+$; wherein R ranges from C$_8$–C$_{20}$ alkyl, preferably C$_{12}$–C$_{15}$ alkyl and M$^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Emcol 4400-1 | Disodium Lauryl Sulfosuccinate | Solid | Witco |
| Witco C5690 | Disodium Cocoamido MEA Sulfosuccinate | Liquid | Witco |
| McIntyre Mackanate CM40F | Disodium Cocoamido MEA Sulfosuccinate | Liquid | McIntyre |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol MEA | Disodium Oleamido MEA | Liquid | Scher |
| Varsulf S13333 | Disodium Ricionoleamido MEA Sulfosuccinate | Solid | Scherex |

Sarcosinates may also be useful in the present invention as a co-active. This category is indicated by the general formula RCON(CH$_3$)CH$_2$CO$_2$—M$^+$, wherein R ranges from C$_8$–C$_{20}$ alkyl, preferably C$_{12}$–C$_{15}$ alkyl and M$^+$ is a sodium, potassium ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W. R. Grace |
| Hamposyl TOC-30 | TEA Cocoyl/Sarcosinate | Liquid | W. R. Grace |

Taurates may also be employed in the present invention as co-actives. These materials are generally identified by the formula RCONR' CH$_2$CH$_2$SO$_3$—M$^+$, wherein R ranges from C$_8$–C$_{20}$ alkyl, preferably C$_{12}$–C$_{15}$ alkyl, R' ranges from C$_1$–C$_4$ alkyl, and M$^+$ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula RN$^+$(CH$_3$)$_2$CH$_2$CO$_2$—M$^+$, amidopropyl betaines of the formula RCONHCH$_2$CH$_2$CH$_2$N$^+$(CH$_3$)$_2$CH$_2$CO$_2$—M$^+$, and amidopropyl sultaines of the formula RCONHCH$_2$CH$_2$N$^+$(CH$_3$)$_2$CH$_2$SO$_3$—M$^+$ wherein R ranges from C$_8$–C$_{20}$ alkyl, preferably C$_{12}$–C$_{15}$ alkyl, and M$^+$ is a sodium, potassium, ammonium or triethanolammonium cation. Typical commercial products representative of these co-actives are found in the Table below:

| Trademark | Chemical Name | Physical Form | Manufacturer |
| --- | --- | --- | --- |
| Tegobetaine F | Cocamidopropyl Betaine | Liquid | Goldschmidt |
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Velvetex OLB-50 | Oleyl Betaine | Paste | Henkel |

Within the broad category of liquid actives, the most effective are the alkyl sulfates, alkyl ether sulfates, alkyl ether sulfonates, sulfosuccinates, and amidopropyl betaines.

Another preferred surfactant is an acyl isethionate having the formula

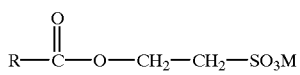

in which R denotes a linear or branched alkyl group and M denotes an alkali metal or alkaline earth metal or an amine.

Another surfactant which may be used are the monoalkyl or dialkylphosphate surfactants.

Another mild surfactant which may be used, preferably used as primary surfactant in combination with other surfactants noted above, is sodium coco glyceryl ether sulfonate. While desirable to use because of its mildness properties, this coco AGS alone does not provide optimum lather creaminess. A sodium 90/10 coconut/tallow alkyl AGS distribution is preferred for creaminess. Salts other than the sodium salt such as TEA—, ammonium, and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines noted above can be used as the sole surfactant, but are more preferred as a co-surfactant. Nonionics generally should not be used as the sole surfactant in this product if high foaming is desirable; however, they can be incorporated as a co-surfactant.

Nonionic and cationic surfactants which may be used include any one of those described in U.S. Pat. No. 3,761, 418 to Parran, Jr., hereby incorporated by reference into the subject application. Also included are the aldobionamides as taught in U.S. Pat. No. 5,389,279 to Au et al; and the polyhydroxy fatty acid amides as taught in U.S. Pat. No. 5,312,934 to Letton, both of which are incorporated by reference into the subject application.

Soaps can be used at levels of about 1 to 10%. Soaps can be used at higher level provided that the surfactant mixture is milder than soap. The soaps may be added neat or made in situ via adding a base, e.g., NaOH; to convert free fatty acids.

Of course, as noted above, soaps should only be used as cosurfactants to the extent that the surfactant system is milder than soap alone.

A preferred surfactant active system is one such that acyl isethionate comprises 1 to 15% by weight of the total composition, an anionic other than acyl isethionate (e.g., ammonium lauryl ether sulfate) comprises 1 to 15% by weight of the total composition and amphoteric comprises 0.5 to 15% by weight of the total composition.

Another preferred active system is one comprising 1 to 20% alkyl ether sulfate. Preferred surfactant active systems may also contain 1 to 10% alkali metal lauryl sulfate or $C_{14}$–$C_{16}$ olefin sulfonate instead of acyl isethionate.

Preferably the surfactant system if used in a liquid cleansing formulation having, for example, from about 10% to about 99% water.

The compositions of the invention preferably comprise anionic surfactants which are not nitrogen-containing anionic surfactants.

Polyvalent Cation or Cations

The second critical component of the liquid compositions of the invention is a polyvalent cation or cations.

Unexpectedly, the addition of certain polyvalent cations was found to provide antibacterial activity when used in the liquid compositions of the invention (whether or not the composition had an antibacterial agent) even though the cations, under conditions used in the invention, did not alone exhibit antibacterial activity (see FIG. 1).

The cations used included zinc, copper, tin, iron, aluminum, cobalt, nickel, chromium, titanium, manganese and mixtures thereof. Particularly preferred cations include zinc and tin.

The metal salts can be provided in any form to the compositions as long as, upon dissolution, the salt will yield polyvalent metal cations or hydrolyzed metal cations in solution.

Another way of saying this, is that the compound yielding the metal cation or cations must be sufficiently water soluble to ensure that the cation or cations are actually released (i.e., available). This is in contrast to insoluble materials such as zinc stearate, magnesium stearate or titanium dioxide which may typically be used for other functions in such cleanser formulations. Typically, such solubility should be higher than 0.01%, preferably higher than 0.05 and more preferably higher than 0.1% solubility in water. There is no criticality as to order of addition or how the salts are added. While not wishing to be bound by theory, it is believed that metals more tightly bound to the salt complex are less effective than those which are not so tightly bound. It is believed there would be fewer metal cations available.

The cation or cations should be delivered in such a way that 0.1 to 10%, preferably 0.1 to 5%, more preferably 0.5 to 5.0% by weight of the compositions comprise the cations.

In a second embodiment of the invention, the liquid skin cleansing compositions of the subject invention contains an antibacterial agent. In this embodiment of the invention, the cation or cations described above not only may provide antibacterial effect on their own, but also enhance (potentiate) the antibacterial effectiveness of the composition.

The antibacterial agent can be present at a level of from about 0.001% to about 5%, typically from about 0.01% to about 2%, and preferably from about 0.01% to about 1.5% by weight of the composition. The level is selected to provide the desired level of antibacterial activity and can be modified as desired. The preferred antibacterial agent is 2-hydroxy-4,2',4'-trichlorodiphenylether (DP300). Other antibacterial agents are set out below. Many antibacterial agents, known to those skilled in the art and disclosed in e.g., U.S. Pat. Nos. 3,835,057 and 4,714,563, both incorporated hereinbefore by reference, may be used.

Antimicrobials

Suitable antibacterial agents which may be used in the subject invention (i.e., in one embodiment of the invention) include:

2-hydroxy-4,2',4'-trichlorodiphenylether (DP300);
2,6-dimethyl-4-hydroxychlorobenzene (PCMX);
3,4,4'-trichlorocarbanilide (TCC);
3-trifluoromethyl-4,4'-dichlorocarbanilide (TFC);
2,2'-dihydroxy-3,3',5,5',6,6'-hexachlorodiphenylmethane;
2,2'-dihydroxy-3,3', 5,5'-tetrachlorodiphenylmethane;
2,2'-dihydroxy-3,3',dibromo-5,5'-dichlorodiphenylmethane;
2-hydroxy-4,4'-dichlorodiphenylether;
2-hydroxy-3,5',4-tribromodiphenlylether; and
1-hydroxyl-4-methyl-6-(2,4,4-trimethyipentyl)-2(1H)-pyridinone (Octopirox).

Other suitable antimicrobials include:

Benzalkonium chloride
Benzethonium chloride
Carbolic acid
Cloflucarbon (Irgasan CF3;4,4'-dichloro-3-(trifluoromethyl) carbanilide)
Chlorhexidine (CHX; 1,6-di(4'-chlorophenyl-diguanido) hexane)
Cresylic acid
Hexetidine (5-amino-1,3-bis(2-ethylhexyl)-5-methylhexahydropyrimidine)
Iodophors
Methylbenzethonium chloride
Povidone-iodine
Tetramethylthiuram disulfide (TMTD; Thiram)
Tribrominated salicylanilide In addition to a mild surfactant compound or compounds; the cation or cations; water; and optionally (or as required in one embodiment), antimicrobial agent, the liquid skin cleansing compositions may contain optionals as described below.

Each of the above components can be incorporated in an aqueous vehicle which may, in addition, include such materials as organic solvents, such as ethanol; thickeners, such as carboxymethylcellulose, magnesium aluminum silicate, hydroxyethylcellulose, methylcellulose or carbopols; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$ EGMS (ethylene glycol monostearate) or Lytron 621 (Styrene/Acrylate copolymer); all of which are useful in enhancing the appearance or cosmetic properties of the product.

The following preservatives may also be used in the liquid skin cleansers of the invention

LIQUID SKIN CLEANSER PRESERVATIVES

| PRESERVATIVE | CHEMICAL NAME |
|---|---|
| Bronopol | 2-Bromo-2nitropropane-1,3,diol |
| Dowicil 200 | cis Isomer of 1-(3-chloroallyl)-3,5,7-triaza-1-azoniaadamantane-chloride OR Quaternium 15 |
| Glycacil | 3-Iodo-2-propynyl butyl carbamate |
| Glydant XL 1000 | DMDM Hydantoin OR dimethyloldimethylhydantoin |

-continued

| PRESERVATIVE | CHEMICAL NAME |
|---|---|
| Glydant Plus | DMDM Hydantoin and 3-iodo-2-propynyl butyl carbamate |
| Formaldehyde | Formaldehyde |
| Germall II | N-(Hydroxymethyl)-N-(1,3-dihydroxymethyl-2,5-dioxo-4-imidazolidinyl)-N'-(hydroxymethyl) urea OR Diazolidinyl urea |
| Germall 115 | N,N'-methylene-bis-[N'-1-(hydroxymethyl)-2,5-dioxo-4-imidazolidinyl]urea OR imidazolidinyl urea |
| Glutaraldehyde | Glutaraldehyde |
| Kathon CG | Mixture of 5-chloro-2-methyl-4-isothiazoline-3-one- and 2-methyl-4-isothiazoline-3-one OR Mixture of methyl, chloromethyl isothiazolinone, and methyl isothiazolinone |
| Parabens | Methyl Paraben, and Ethyl Paraben, and Propyl Paraben and Butyl Paraben OR those esters of p-hydroxybenzoic acid |
| Phenoxyethanol | 2-Phenoxyethanol |
| Salicylic Acid | Salicylic Acid OR o-Hydroxybenzoic acid |
| Sorbic Acid | Sorbic Acid, Potassium Sorbate |

Coconut acyl mono- or diethanol amides as suds boosters, and strongly ionizing salts such as sodium chloride and sodium sulfate may be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24 and Merquat Plus 3330—Polyquaternium 39.

Polyethylene glycols which may be used included:

| Polyox | WSR-205 | PEG 14M, |
| Polyox | WSR-N-60K | PEG 45M, or |
| Polyox | WSR-N-750 | PEG 7M. |

Thickeners which may be used include Americoll Polymer HM 1500 (Nonoxynyl Hydroethyl Cellulose); Glucan DOE 120 (PEG 120 Methyl Glucose Dioleate).

In a third embodiment of the invention, the invention is concerned with a method of improving the antimicrobial effectiveness of mild, antimicrobial, liquid cleansing compositions which method comprises adding 0.1 to 10% by wt. of a polyvalent cation or cations to a composition comprising 1 to 99% of a surfactant system and 1 to 99% water, wherein greater than 10% of the surfactant is anionic surfactant.

Unless stated otherwise, the percentages in the specification, examples and claims are percentages by weight.

The following examples are intended for illustrative purposes only and should not be construed to limit the invention in any way.

EXAMPLES

An In vitro Bactericidal Kill Test is used to measure antimicrobial activity in the examples which follow. Methodology for the test is set forth below:

In Vitro Bactericidal Kill Test

An in vitro bactericidal test was used to determine the antibacterial effect of products on Staphylococcus aureus ATCC #6538 during a short contact time. One milliliter (about 108 cells) of bacteria was exposed for one minute to a one-percent solution of liquid skin cleansing composition. The sample was added to additional water, mixed, and further diluted in 0.1% peptone. Duplicate samples of appropriate dilutions were plated on neutralizing media. In addition, the bacterial culture was plated to determine the actual number of organisms inoculated. The plates were incubated at 34° C. for 48 hours and enumerated. The CFU/ml (colony forming units per milliliter) from dilutions with plate counts in the range of 30–300 were averaged together to produce the final CFU/ml.

The results may be expressed as the log of the CFU/ml. The culture control indicates the actual number of bacteria inoculated while the water control reflects the number of organisms recovered in the absence of product. The lower the number, the more effective the solution was in killing the bacteria.

In this assay, a sampling error of approximately 0.5 log is likely, therefore differences of 0.5 log between products may not be significant. As a result, the data should be viewed in terms of trends rather than as absolute numbers.

Example 1

Applicants tested the effect of a variety of metal salts (2% additive) in (1) water, and (2) a full liquid skin cleansing formulation as set forth below

| INGREDIENT | % BY WEIGHT |
| --- | --- |
| Acyl Isethionate | 1–15% |
| Anionic other than Acyl Isethionate (SLES)* | 1–15% |
| Amphoteric Surfactant** | 5–15% |
| Cation or Cations | 0.5 to 5% |
| Sequestrant (EDTA or EHDP) | 0.01–0.1% |
| Moisturizer (e.g. cationic polymer) | 0.05–3.0% |
| Standard additives (e.g., dyes, perfumes) | 0–10% |
| DP300 (Triclosan) | .1–1% |
| Water | Balance |

*Sodium lauryl ether sulfate
**Cocamidopropyl betaine

The bacterial activity of the additive salts was set forth for each salt in Table 1 below:

| Additive | Sample pH | Δlog (CFU/ml) |
| --- | --- | --- |
| Metal Salts | | |
| AlCl$_3$ | 3.50 | 1.76 |
| Ba(acetate)$_2$ | 6.25 | −0.70 (Comparative) |
| CuCl$_2$ | 4.60 | 3.51 |
| FeSO$_4$* | 5.50 | 1.46 |
| KCl | 6.35 | 0.02 (Comparative) |
| NaCl | 5.50 | 0.15 (Comparative) |
| SnF$_2$* | 5.17 | 2.77 |
| SrCl$_2$ | 5.52 | 0.06 (Comparative) |
| Znacetate | 5.93 | 0.90 |
| Zncitrate | 5.50 | 0.86 |
| ZnCl | 5.53 | 0.99 |
| ZnO | 7.73 | 0.87 |
| ZnSO$_4$ | 5.54 | 1.05 |
| Znstearate | 5.99 | 0.05 (Comparative) |
| CoCl$_2$ | 5.27 | 0.95 |
| MnCl$_2$ | 5.27 | 1.05 |
| NiCl$_2$ | 5.44 | 1.31 |
| CrCl$_2$* | 5.47 | 1.87 |
| Zn lauroyl lactylate | 5.68 | 1.80 |

The bactericidal activity is represented as a difference in the log of cell counts of the sample from that of liquid Lever 2000 [represeted as Δlog (CFU/ml)]. Therefore, a large number indicates higher antibacterial activity. A representative value is given for sample pH.
*sample pH adjusted with 0.1N NaOH.

FIG. 1 shows that metal ion itself has no antibacterial activity in water; that the cleansing formulation has low activity; but that the combination shows strong antibacterial activity.

Example 2

Dose Response

In order to determine how dose response affected bacterial activity in the formulation of Example 1, applicants tested various concentrations of ZnCl$_2$ in the formulation. The results are set forth in FIG. 2.

Figure 2:
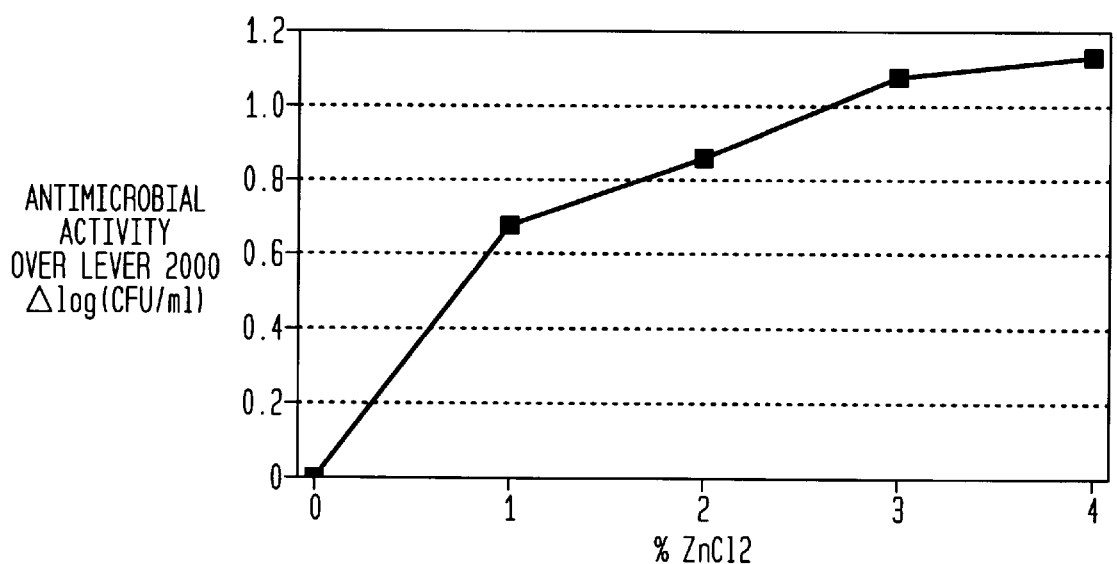
FIG. 2 shows the effect of various dose concentrations of zinc cations (delivered in $ZnCl_2$) on the antimicrobial activity of a typical, mild skin cleansing formulation of the invention.

As seen from FIG. 2, the antibacterial activity in the composition increases with increasing dosage. As noted, dose response started to level off at about 5%.

Example 3

In order to show that the invention works in different formulations as well as in formulations which may or may not contain an antibacterial agent, applicants tested the compound or compounds of the invention in several commercial compositions. The results are set forth in FIG. 3.

The various compositions tested are set forth below. The first composition was the composition of Example 1.

Figure 3:
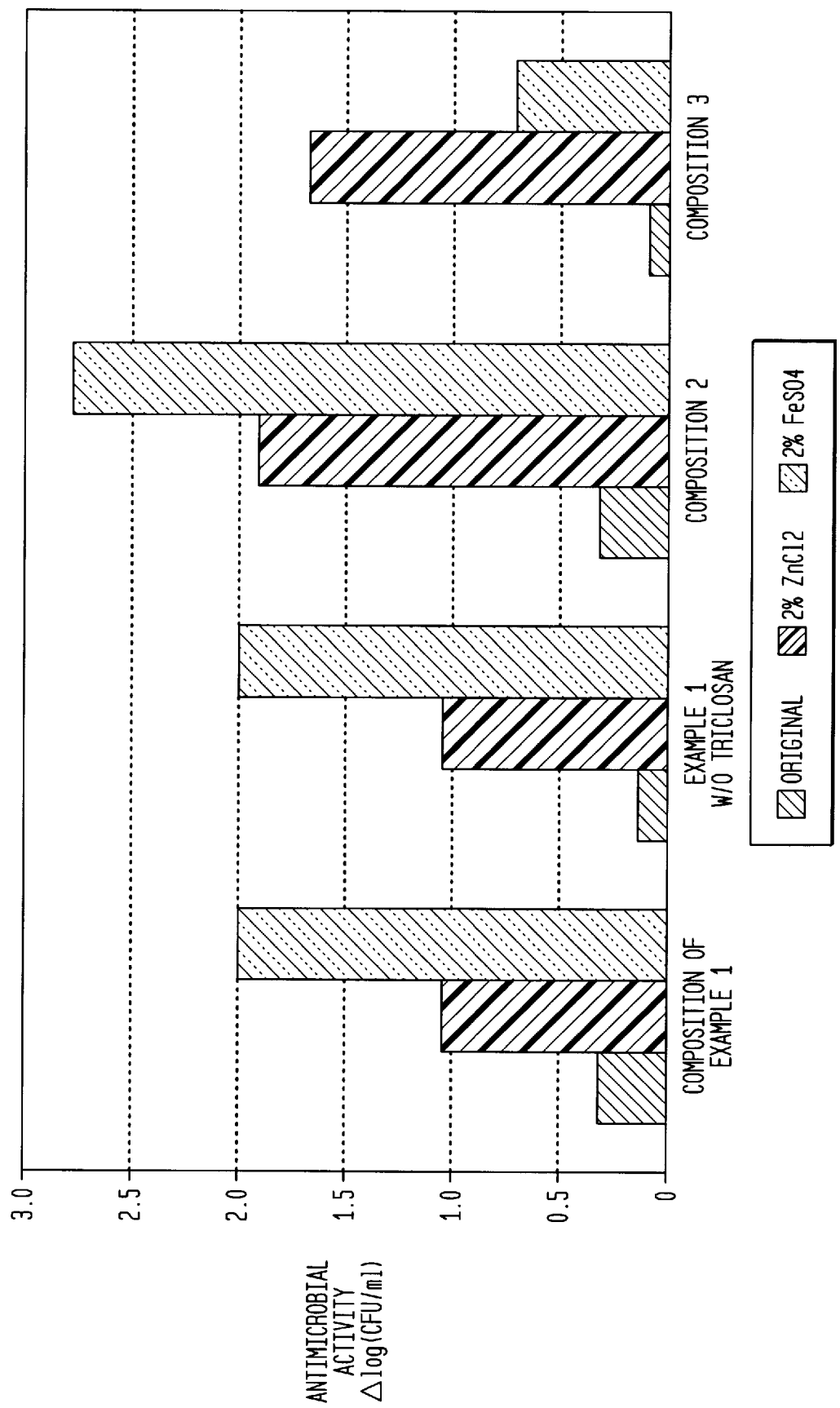
FIG. 3 shows antibacterial effect (measured by change in log (CFU/ml) of zinc and iron cations on a typical, mild skin cleansing formulation, both with and without antibacterial agent (e.g., Triclosan or DP300$^R$); as well as the effect on two other mild formulations. The higher the $\Delta$log (CFU/ml), the greater the antibacterial activity.
Figure 4:
FIG. 4 shows that the metal cations of the invention show low levels of zein solubilization (i.e., are mild) when added to a typical mild cleansing composition.

The estimated composition or list of ingredients for compositions 2 and 3 in FIG. 3 is set forth below:

| Composition 2* (Estimated Ingredients) | Estimated % by wt. |
| --- | --- |
| Ammonium Lauryl Sulfate | 6.6 |
| Sodium Laureth Sulfate | 5.2 |
| Lauramide DEA | 3.5 |
| Glycerin | 1.5 |
| Isostearamidopropyl Morpholine Lactate | 0.6 |
| Citric Acid | 0.2 |
| Disodium Ricinoteamido MEA Sulfosuccinate | 0.1 |
| Triclosan | 0.2 |
| Water | 80.9 |
| Dyes, EDTA, Hydantoin | |

*Liquid Dial Antibacterial Soap

| Composition 3* | Estimated % by Wt. |
| --- | --- |
| Glycerin | 19.5 |
| Sodium Soap | 14.1 |
| Disodium Lauroamphodiacetate | 3.5 |
| Cocamidopropyl Betaine | 1.5 |
| Lauramide DEA | 2.0 |
| Triethanolamine | 0.9 |
| Water | 55.7 |
| BHT | Minor |
| Citric Acid | Minor |
| Methylparaben | Minor |

| | |
|---|---|
| Trisodium HEDTA | Minor |
| Propylparaben | Minor |
| Colorants | Minor |
| Perfume | Minor |

*Neutrogena

Example 4

Zein Solubilization Assay

In vitro "Mildness" Test/Assesssing Mildness

It is generally believed that surfactants are irritants because they penetrate the stratum corneum and then react with the inner cells of the epidermis.

Traditionally, the study of percutaneous absorption has focused on measuring the diffusion of chemicals through the stratum corneum.

We have obtained information on mildness potentials of the compositions of the invention through the use of in vitro tests which have been demonstrated to correlate well with in vivo tests.

Gotte in Proc. Int. Cong. Surface Active Subs., 4th Brussels (1964), 3, 83–90 and Schwinger in Kolloid-Z. Z. Poly., (1969), 233, 898 have shown that the ability to solubilize zein, an insoluble maize protein, correlates well with irritation potential.

More specifically, the greater the zein solubilization, the greater the irritation potential of a composition.

Example 5

In order to determine whether the cation or cations of the invention had a negative effect on foam height, the composition of Example 1 was tested with various salts. Foam height was measured by the method described in ASTM D 1173-53 hereby incorporated by reference into the subject application. More particularly, foaming ability of 1% liquid skin cleansing formulations was measured by dripping 200 ml of the solution from Miles pipet onto 50 mL of the solution in a glass cylinder as specified in ASTM D1173-53. Foam height readings were taken after 1 minute and 5 minutes at 25° C. As seen in FIG. 5, foam height remained almost the same.

Example 6

The compound or compounds of the invention may also be used in the following formulations.

| Component | % by Weight |
|---|---|
| FORMULATION 1 | |
| Sodium Isethionate | 3–5% |
| Sodium Alkene Benzene Sulfonate | 1–3% |
| Sodium Laureth Sulfate | 3–5% |
| Sodium Cocoyl Isethionate | 8–12% |
| Sodium Tallow/Coconut Soap | 1-3% |
| Preservative (e.g., Methylparaben) | .1–.5% |
| Sequestrants | .01–.05% |
| Fatty Acid (e.g. Stearic Acid) | 7–10% |
| Sulfosuccinate | 3–5% |
| Water plus minors | to balance |
| FORMULATION 2 | |
| Sodium Cocoyl Isethionate | 5–8% |
| Cocamidopropyl Betaine | 5–8% |
| Sulfosuccinate | 2–5% |
| Fatty Acid | 6–9% |
| Sodium Isethionate | 1–3% |
| Silicone Emulsion | 3–7% |
| Sequestrant | .01–.05 |
| Water plus minors | to balance |

We claim:

1. A liquid skin cleansing composition comprising:

(a) about 3% to about 40% by weight of a surfactant system comprising an acyl isethionate, an anionic surfactant other than acyl isethionate and an amphoteric surfactant, wherein one or more surfactants which alone or together are milder than soap itself when measured percent zein dissolved;

(b) 0.1 to 10% by weight of a polyvalent cation or cations selected from the group consisting of copper, tin, iron, cobalt, nickel, chromium, titanium and/or manganese and mixtures thereof;

(c) 0.001% to about 5% by weight of an antibacterial agent; and (d) about 60% to about 97% by weight water;

wherein greater than 10% to 100% of the surfactant system is an anionic surfactant.

2. A composition according to claim 1, wherein the surfactant system comprises 1 to 15% by wt. isethionate.

3. A composition according to claim 1, wherein the surfactant system comprises 1 to 15% of an anionic other than acyl isethionate and 0.5 to 15% by wt. amphoteric.

4. A composition according to claim 1, wherein the surfactant system comprises 1 to 20% alkyl ether sulfate.

* * * * *